(12) United States Patent
Park et al.

(10) Patent No.: US 11,090,145 B2
(45) Date of Patent: Aug. 17, 2021

(54) DEVICE FOR DELIVERING GRAFTS AT A SURGICAL SITE AND METHOD

(71) Applicant: Park Surgical Innovations, LLC, Peachtree Corners, GA (US)

(72) Inventors: David D. Park, Peachtree Corners, GA (US); Ashley B. Hancock, Atlanta, GA (US); Byron F. Smith, Nashville, TN (US); Tanner Hargens, Brentwood, TN (US)

( * ) Notice: Subject to any disclaimer, the term of this patent is extended or adjusted under 35 U.S.C. 154(b) by 0 days.

(21) Appl. No.: 16/571,696

(22) Filed: Sep. 16, 2019

(65) Prior Publication Data

US 2020/0008920 A1 Jan. 9, 2020

Related U.S. Application Data

(63) Continuation-in-part of application No. 16/029,447, filed on Jul. 6, 2018, now Pat. No. 10,898,310.

(Continued)

(51) Int. Cl.
*A61F 2/00* (2006.01)
*A61B 17/34* (2006.01)
*A61M 25/00* (2006.01)

(52) U.S. Cl.
CPC ........ *A61F 2/0063* (2013.01); *A61B 17/3468* (2013.01); *A61F 2002/0072* (2013.01);
(Continued)

(58) Field of Classification Search
CPC .......... A61B 17/3468; A61B 2017/003; A61B 2017/00318–00336;
(Continued)

(56) References Cited

U.S. PATENT DOCUMENTS

| 5,147,316 A | 9/1992 | Castillenti |
| 5,379,754 A | 1/1995 | Tovey et al. |

(Continued)

FOREIGN PATENT DOCUMENTS

| EP | 1224919 | 7/2002 |
| EP | 1408846 | 3/2012 |

(Continued)

OTHER PUBLICATIONS

Theodore R. Kucklick; Basics of Catheter Assemby; The Medical Device R&D Handbook, Second Edition; 2013; pp. 107-125.

(Continued)

*Primary Examiner* — Katherine H Schwiker
*Assistant Examiner* — Alexis D Amechi
(74) *Attorney, Agent, or Firm* — B. Craig Killough; Hellman & Yates, PA

(57) ABSTRACT

A device and method for delivering a synthetic mesh or graft for anatomical repair at a defect site. A plurality of flexible arms is connected to the synthetic mesh or graft. Grasping jaws are individually controlled at or near a proximal end of the device for connection of the graft and release of the graft at the surgical site. The flexible arms, with graft attached are positioned through a surgical incision to the defect site. An actuator positions the flexible arms to assume a radial array at the surgical site, unfolding and spreading the graft for attachment. The length of each flexible arm is individually adjustable to adapt to the size and shape of the graft selected for installation at the defect site to repair the defect.

16 Claims, 20 Drawing Sheets

Related U.S. Application Data

(60) Provisional application No. 62/529,262, filed on Jul. 6, 2017.

(52) U.S. Cl.
CPC .. *A61F 2210/0014* (2013.01); *A61M 25/0074* (2013.01); *A61M 25/0082* (2013.01)

(58) Field of Classification Search
CPC . A61B 2017/00367–00384; A61B 2017/2912; A61B 2017/2924; A61B 2017/2905; A61B 2017/2906; A61B 2017/2908; A61B 17/221; A61F 2002/0072; A61F 2/0063; A61F 2/95; A61F 2002/9528; A61F 2002/9534
See application file for complete search history.

(56) References Cited

U.S. PATENT DOCUMENTS

| | | | |
|---|---|---|---|
| 5,405,360 A | 4/1995 | Tovey | |
| 5,957,939 A | 9/1999 | Heaven et al. | |
| 6,425,924 B1 | 7/2002 | Rousseau | |
| 6,478,803 B1 | 11/2002 | Kapec et al. | |
| 6,669,735 B1 | 12/2003 | Pelissier | |
| 7,662,112 B2 | 2/2010 | Zamierowski et al. | |
| 7,947,054 B2 | 5/2011 | Eldar et al. | |
| 7,963,992 B2 | 6/2011 | Cauthen, III et al. | |
| 8,097,008 B2 | 1/2012 | Henderson | |
| 8,518,024 B2* | 8/2013 | Williams | A61B 1/00128 606/1 |
| 8,579,989 B2 | 11/2013 | Leahy | |
| 8,616,460 B2 | 12/2013 | Kurtz et al. | |
| 8,641,699 B2 | 2/2014 | Hansen | |
| 9,339,365 B2 | 5/2016 | Park et al. | |
| 2005/0256532 A1 | 11/2005 | Nayak et al. | |
| 2006/0015142 A1 | 1/2006 | Malazgirt | |
| 2007/0185506 A1 | 8/2007 | Jackson | |
| 2008/0195121 A1 | 8/2008 | Eldar et al. | |
| 2009/0254103 A1 | 10/2009 | Deutsch | |
| 2009/0312645 A1* | 12/2009 | Weitzner | A61B 1/00098 600/476 |
| 2010/0069930 A1 | 3/2010 | Roslin et al. | |
| 2010/0069947 A1 | 3/2010 | Sholev et al. | |
| 2010/0130850 A1 | 5/2010 | Pakter | |
| 2010/0179579 A1 | 7/2010 | Halevy | |
| 2011/0015491 A1* | 1/2011 | Ravikumar | A61B 1/32 600/233 |
| 2011/0054500 A1 | 3/2011 | Levin et al. | |
| 2011/0184459 A1 | 7/2011 | Malkowski et al. | |
| 2011/0196392 A1 | 8/2011 | Saadat et al. | |
| 2012/0016409 A1 | 1/2012 | Sherwinter et al. | |
| 2012/0095451 A1 | 4/2012 | Hegemann et al. | |
| 2012/0190924 A1 | 7/2012 | Tseng | |
| 2013/0012958 A1 | 1/2013 | Marczyk et al. | |
| 2013/0018402 A1* | 1/2013 | Polo | A61B 17/32056 606/170 |
| 2014/0107675 A1 | 4/2014 | Hansen | |
| 2014/0276914 A1* | 9/2014 | Hayashida | A61B 17/08 606/119 |
| 2015/0100117 A1* | 4/2015 | Bortlein | A61B 17/00234 623/2.11 |
| 2015/0119851 A1* | 4/2015 | Hoogenakker | A61B 17/00234 604/507 |
| 2016/0051280 A1* | 2/2016 | Dejima | A61B 17/0218 600/114 |
| 2017/0172551 A1 | 6/2017 | Rao | |

FOREIGN PATENT DOCUMENTS

| | | |
|---|---|---|
| EP | 2617350 | 12/2014 |
| EP | 2729077 | 7/2018 |
| WO | WO 2012128591 | 12/2012 |
| WO | WO 2013009699 | 1/2013 |
| WO | WO 2013154700 | 10/2013 |

OTHER PUBLICATIONS

Filip Jelinek, Ewout A. Arkenbout, Paul W.J. Henselmans, Rob Pessers, Paul Breedveld; Classification of Joints Used in Steerable Instruments for Minimally Invasive Surgery—A Review of the State of the Art; Journal of Medical Devices, Mar. 2015, vol. 9; pp. 010801-1-010801-11.

Bard Kugel Hernia Repair Featuring Onflex Mesh Technique Guide Posterior Approach to an Preperitoneal Inguinal Hernia Repair, 2016.

\* cited by examiner

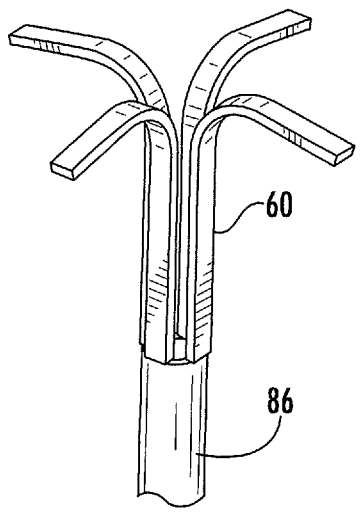
FIG. 18
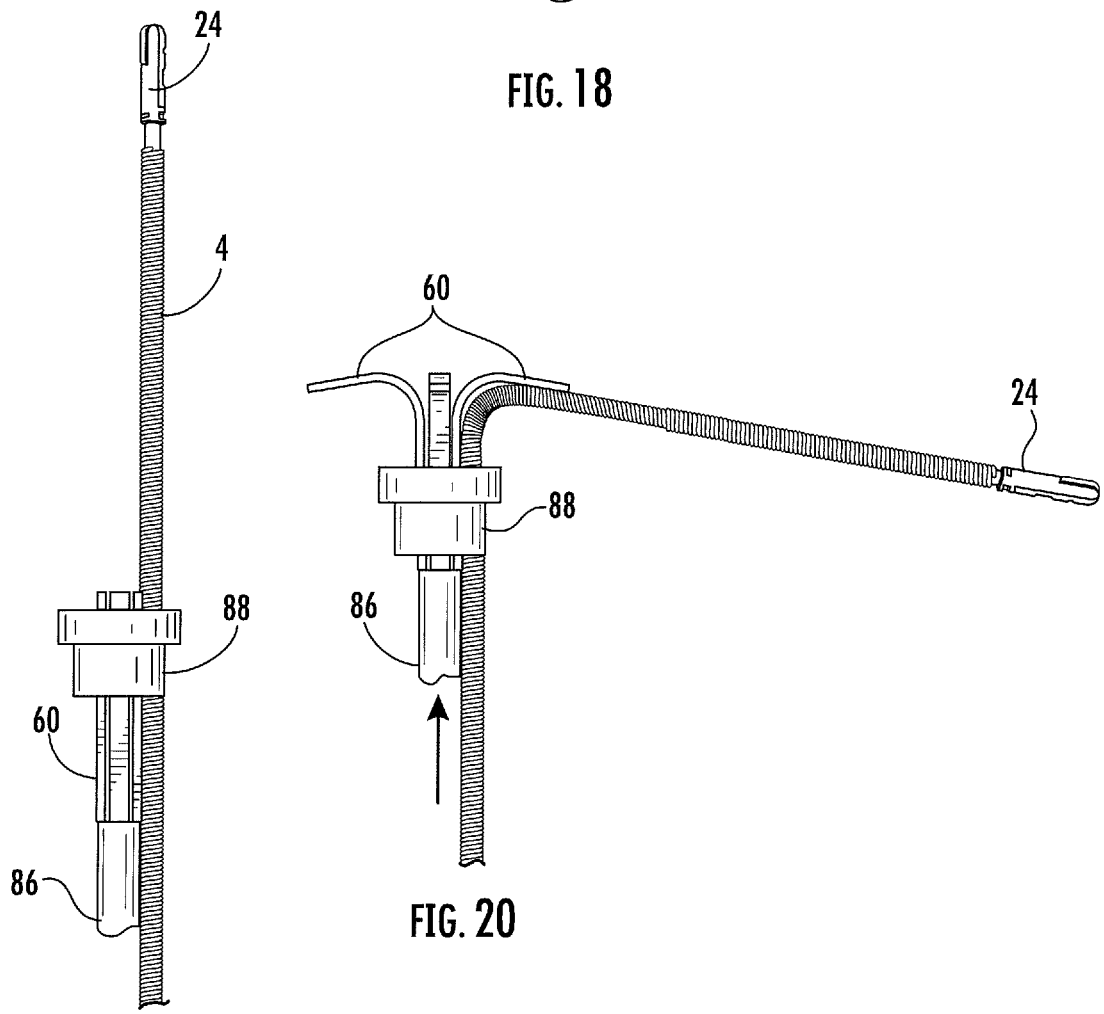
FIG. 19
FIG. 20

DEVICE FOR DELIVERING GRAFTS AT A SURGICAL SITE AND METHOD

This is a continuation in part of application Ser. No. 16/029,447 filed Jul. 6, 2018.

Applicant claims the benefit of U.S. Provisional Application Ser. No. 62/529,262 filed Jul. 6, 2017.

BACKGROUND OF THE INVENTION

Biological grafts and synthetic mesh are used to repair anatomical defects, such as hernias. Delivery of the mesh or graft into body cavities either requires invasive surgery, or heretofore unsatisfactory laparoscopic methods.

Hernias are structural defects most commonly involving the musculofascial tissues of the abdominal and pelvic regions within the human body. Most hernias eventually require surgical repair. Surgical repair of ventral incisional hernias may be accomplished via an "open method." This method involves making a sizable incision directly over the tissue defect, separating the contents of the hernia away from the musculofascial defect, and repairing the defect primarily using sutures, or more commonly, sewing a graft to the defect edge in tension-free manner. This is done in an effort to minimize the recurrence of hernia formation which may occur with some frequency. The recurrence may be due to multiple factors including general health of the patient, surgical technique, and types of mesh or graft utilized. Overall, this traditional method is effective, but also often involves more pain, long periods of disability following the surgery, higher perioperative infection rates, and an established hernia recurrence rate.

Alternatively, ventral incisional hernias may be repaired using the "laparoscopic method." However, this method has its own set of major shortcomings principally related to higher degree of difficulty in performing this procedure. One of the major challenges involve graft introduction into the abdominal cavity. Typically, a graft is rolled tightly into a cylindrical configuration and subsequently, pushed/pulled through the trocar which can be both time consuming and frustrating, especially when a larger graft is needed to cover the defect. This maneuver can also damage the graft during the delivery due to excessive force used or needed during the delivery process. Some surgeons also elect to place multiple sutures within the periphery of the graft for transfascial securement. This is often done prior to introduction of the graft. Once delivered into the abdominal cavity, the rolled graft/suture combination is unrolled, sutures isolated into respective corresponding abdominal quadrants, and the graft is centered over the defect prior to fixation. These steps are often very challenging and frustrating to accomplish in an efficient manner due to the pliable property of the graft and sutures which is a desired characteristic.

SUMMARY OF THE INVENTION

The present invention is a device and method for delivering a synthetic mesh or graft for anatomical repair at a defect site. A plurality of flexible arms is connected to the synthetic mesh or graft. Grasping jaws are individually controlled at or near a proximal end of the device for connection of the graft and release of the graft at the surgical site. The flexible arms, with graft attached are positioned through a surgical incision to the defect site. An actuator positions the flexible arms to assume a radial array at the surgical site, unfolding and spreading the graft for attachment. The length of each flexible arm is individually adjustable to adapt to the size and shape of the graft selected for installation at the defect site to repair the defect.

BRIEF DESCRIPTIONS OF THE DRAWINGS

Figure 6A:
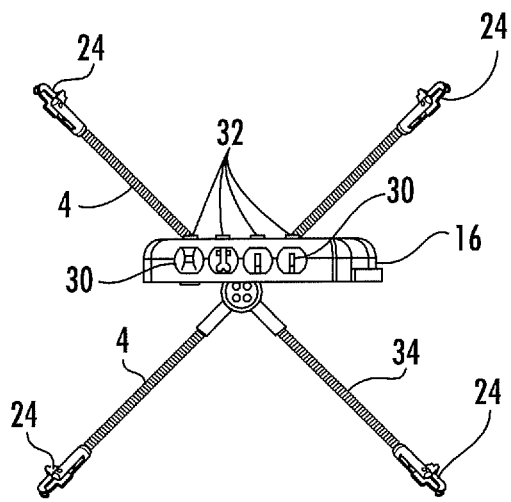
FIG. 6A is an elevation of an embodiment of the invention taken from a proximal end of the invention.
Figure 6B:
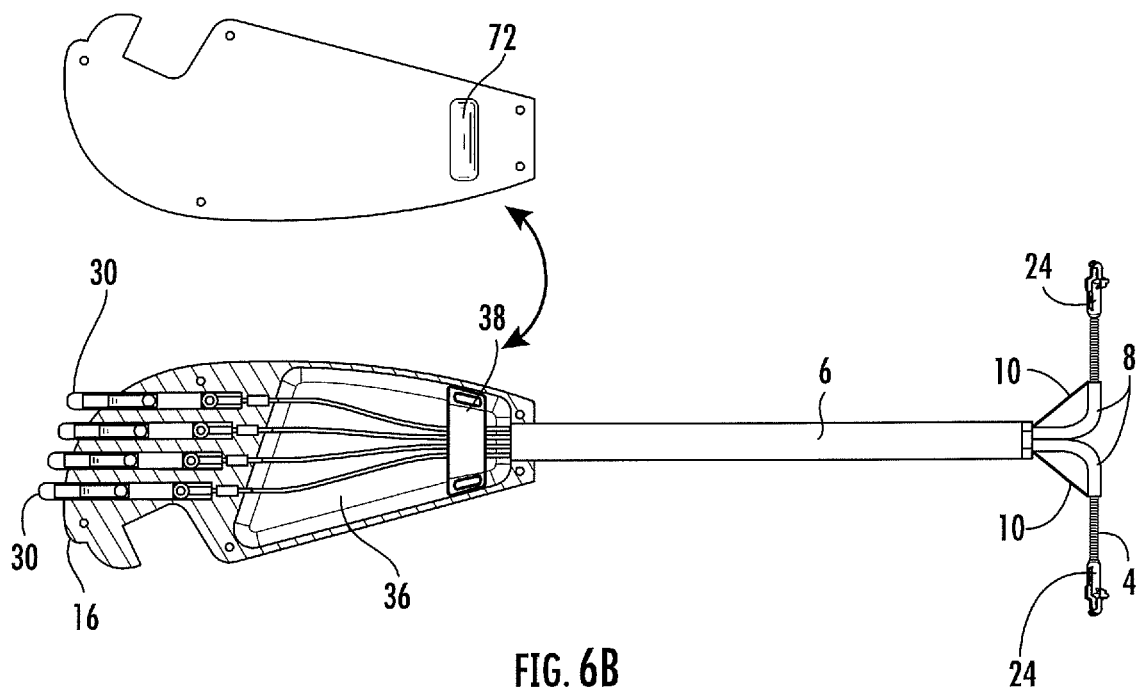

FIG. 6B demonstrates a cover for the housing removed from the device.

Figure 7:
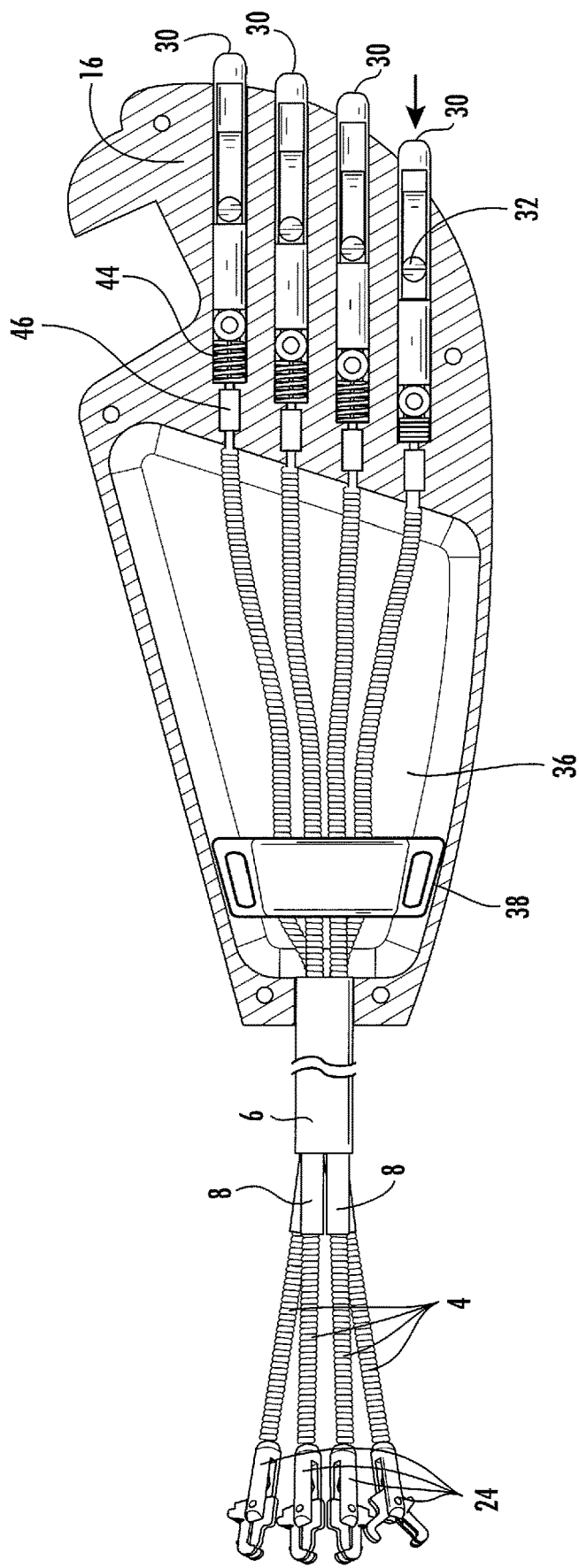

FIG. 7 is an elevation of one side of an embodiment of the invention with the cover removed from housing 16.

Figure 8:
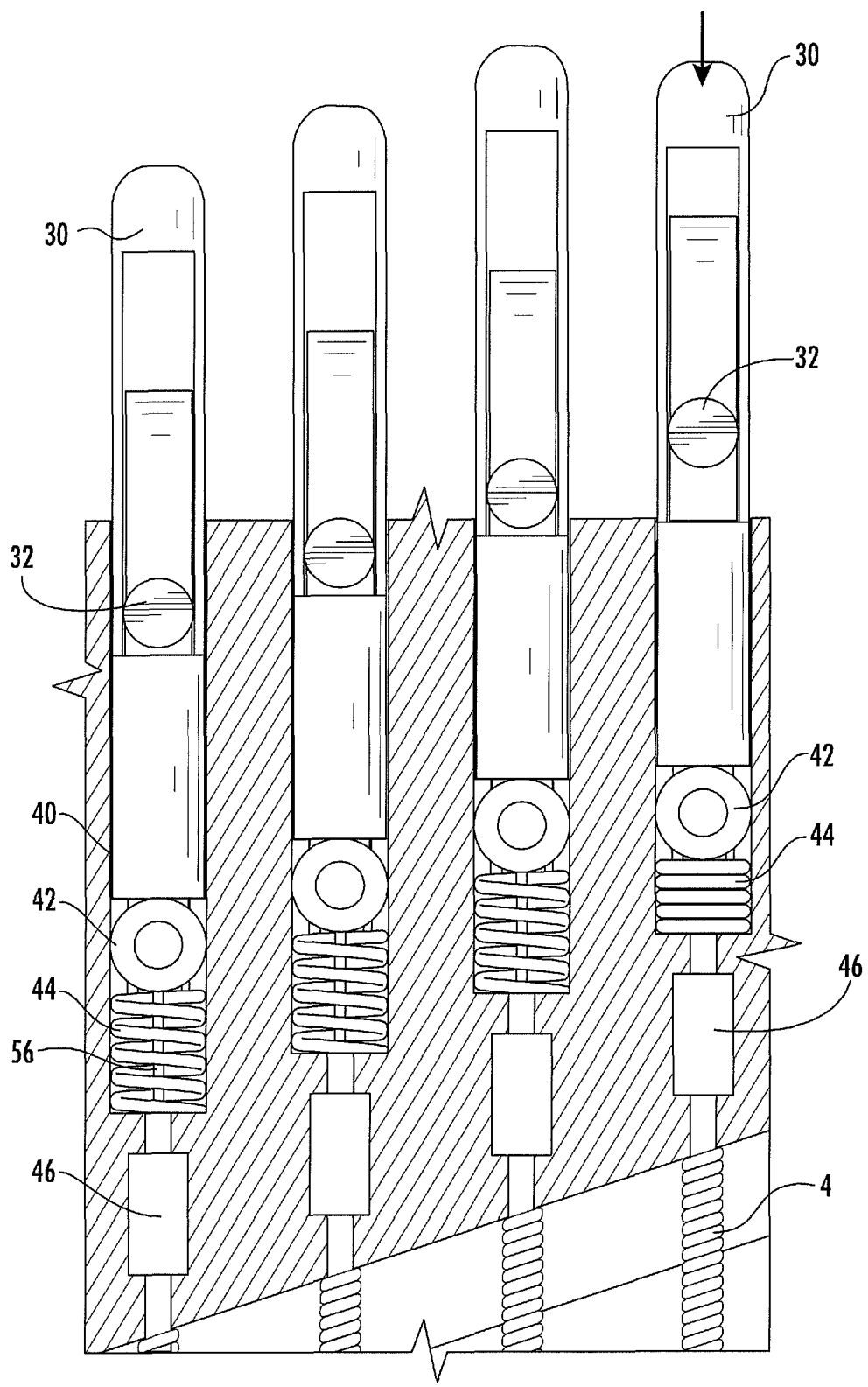

FIG. 8 is an enlarged isolation of a portion of the actuators for grasping jaws 24.

Figure 9:
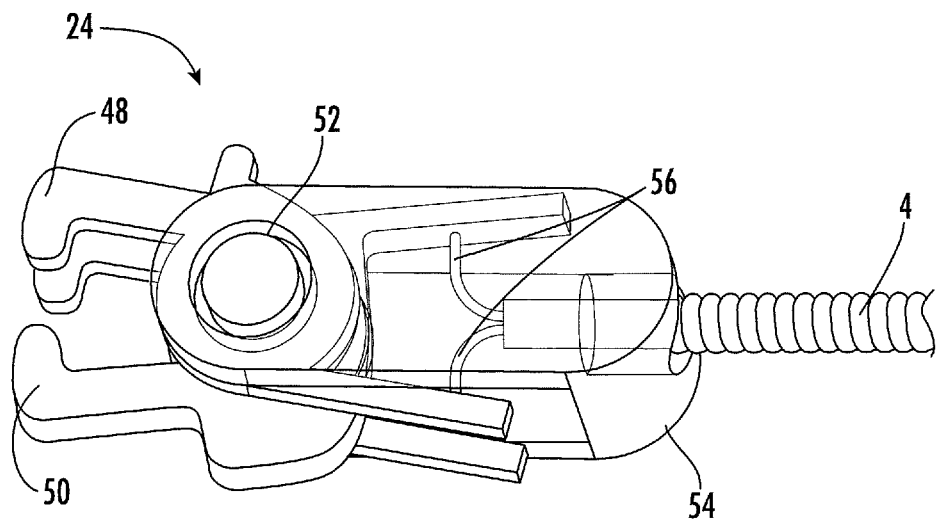

FIG. 9 is an isolation of an embodiment of a grasping jaw 24.

Figure 10A:
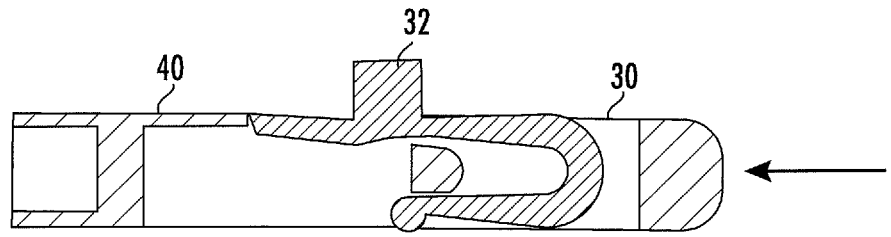
Figure 10B:
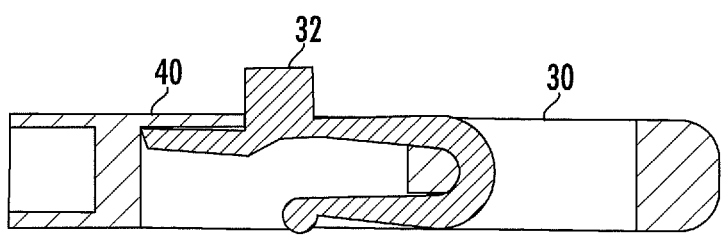

FIG. 10A and FIG. 10B are isolations of a portion of the actuator for the grasping jaws sectioned to demonstrate the action of release button 32.

Figure 11A:
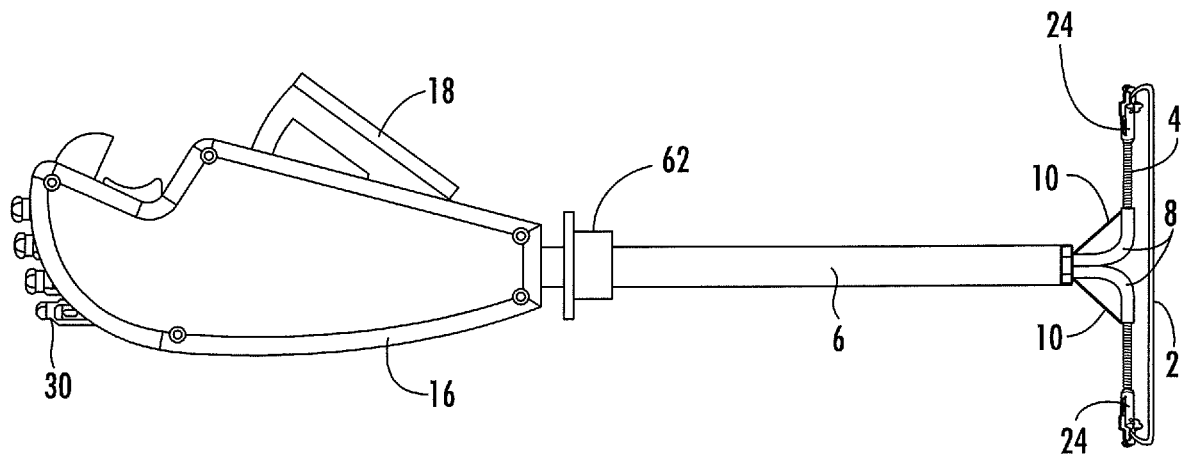

FIG. 11A shows the device according to an embodiment of the invention with a graft affixed to it.

Figure 11B:
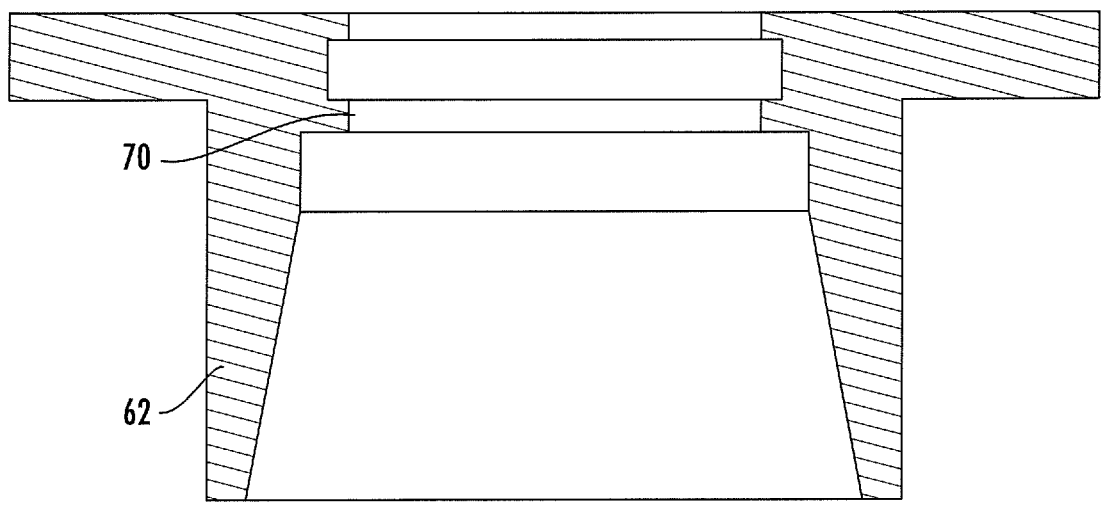

FIG. 11B is a side sectioned view of a seal that slidably attaches to a shaft of the device for sealing a trocar.

Figure 12:
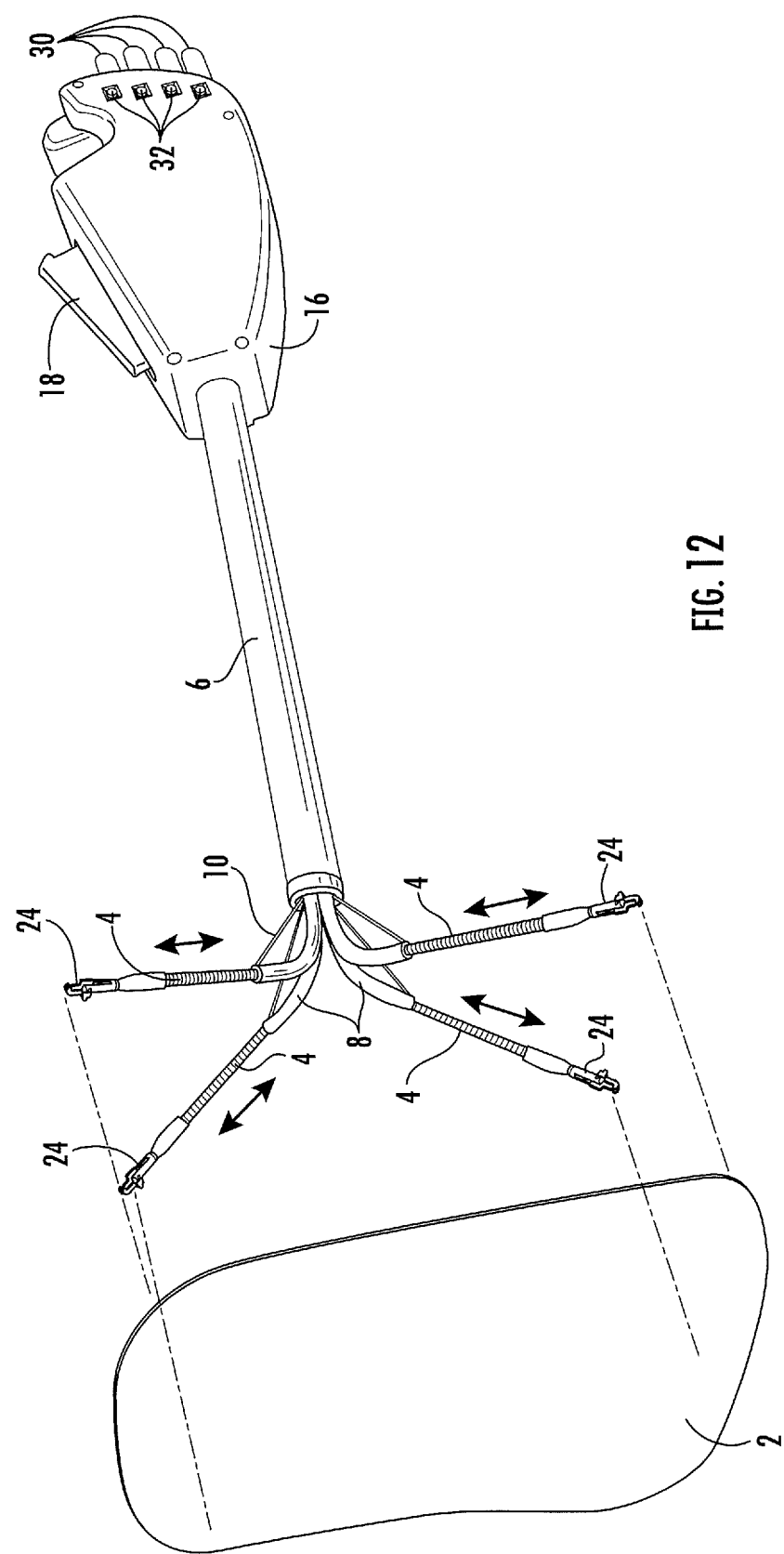

FIG. 12 demonstrates attachment of the graft to the embodiment of the device as shown in the drawing figures.

Figure 13A:
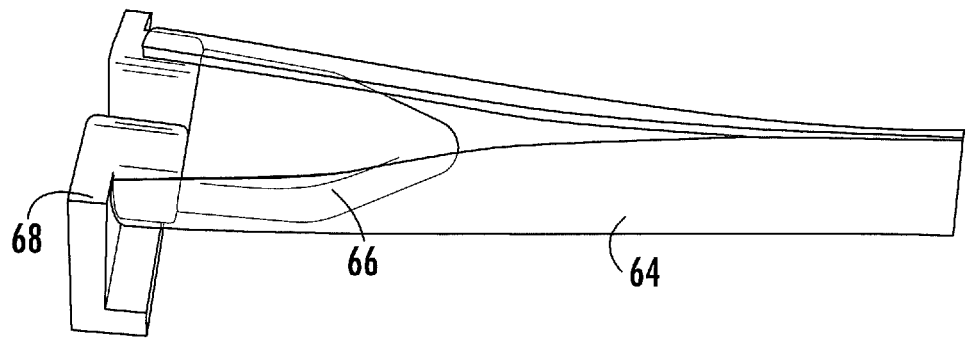

FIG. 13A shows a sheath that covers the graft to facilitate insertion of the graft and a portion of the device through a trocar and into the surgical site.

Figure 13B:
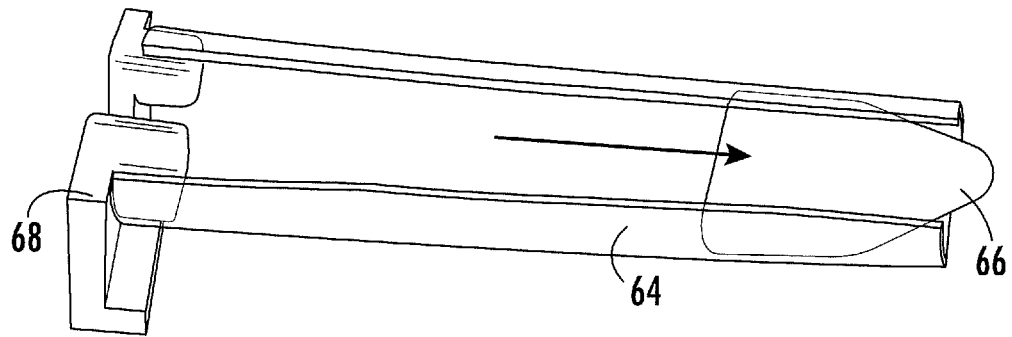

FIG. 13B demonstrates a step of opening of a split in the sheath for insertion of the device with graft into the sheath.

Figure 13C:
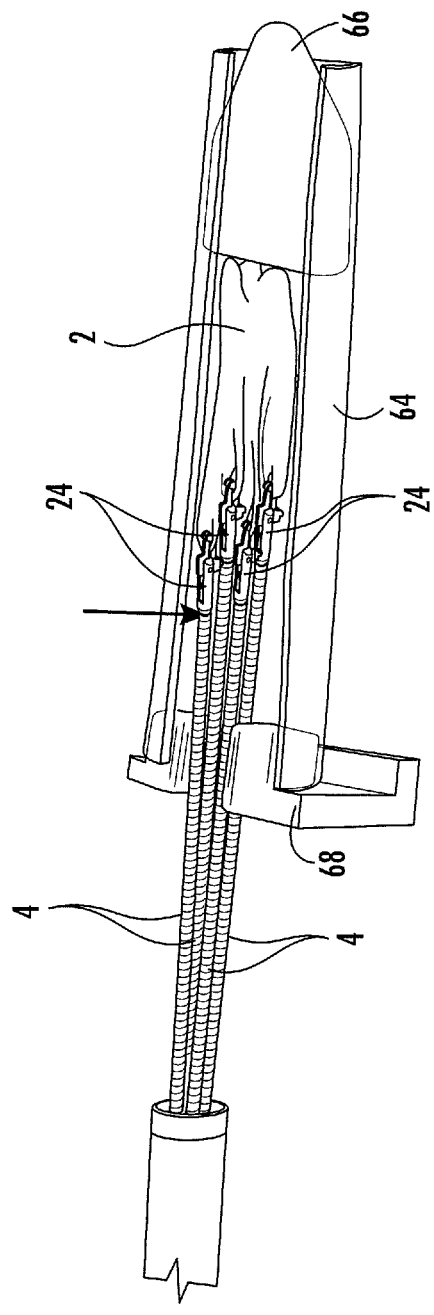

FIG. 13C shows the step of positioning the device with graft into the sheath.

Figure 13D:
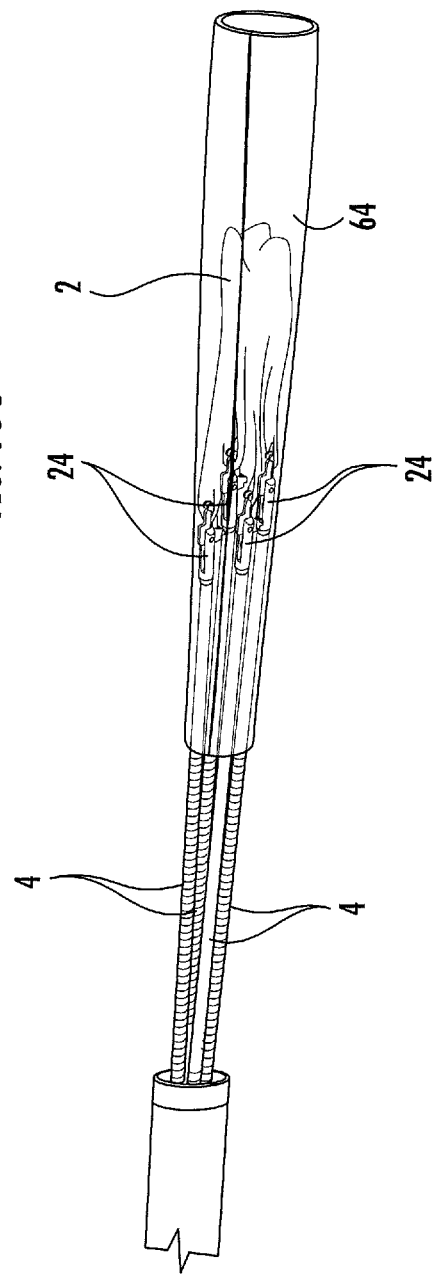

FIG. 13D shows the device with graft in the sheath and surrounding the sheath.

Figure 14A:
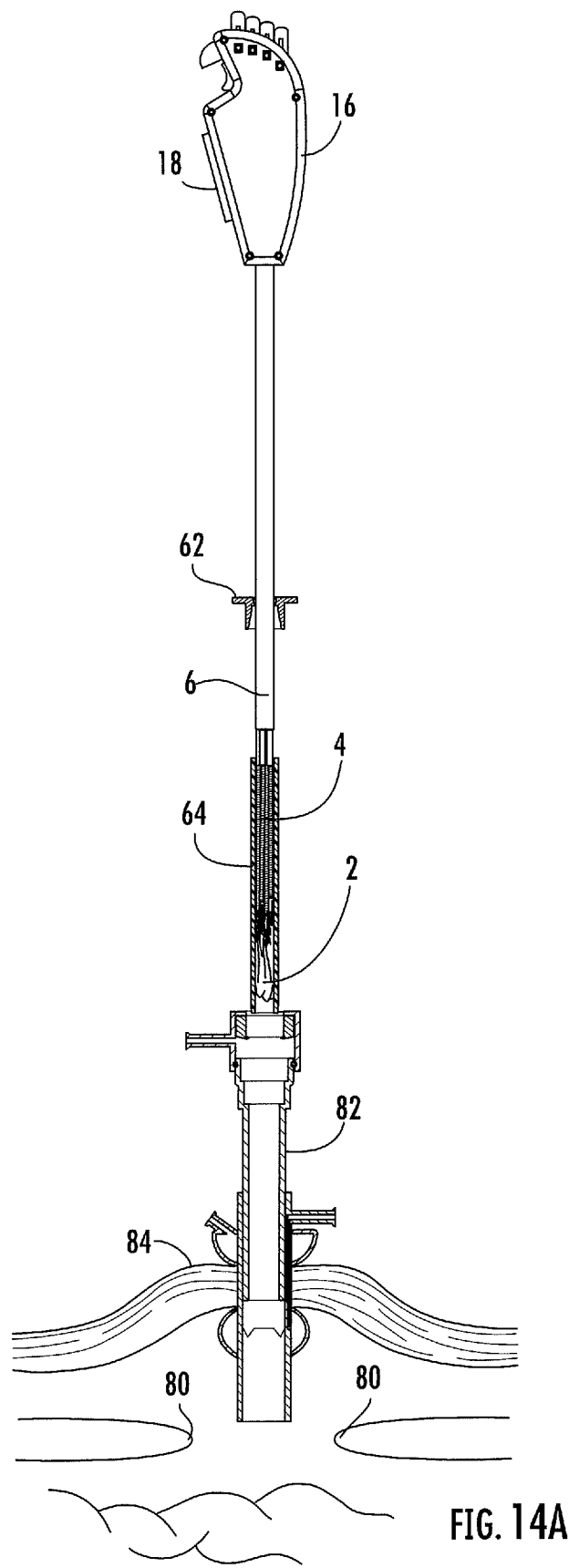
Figure 14B:
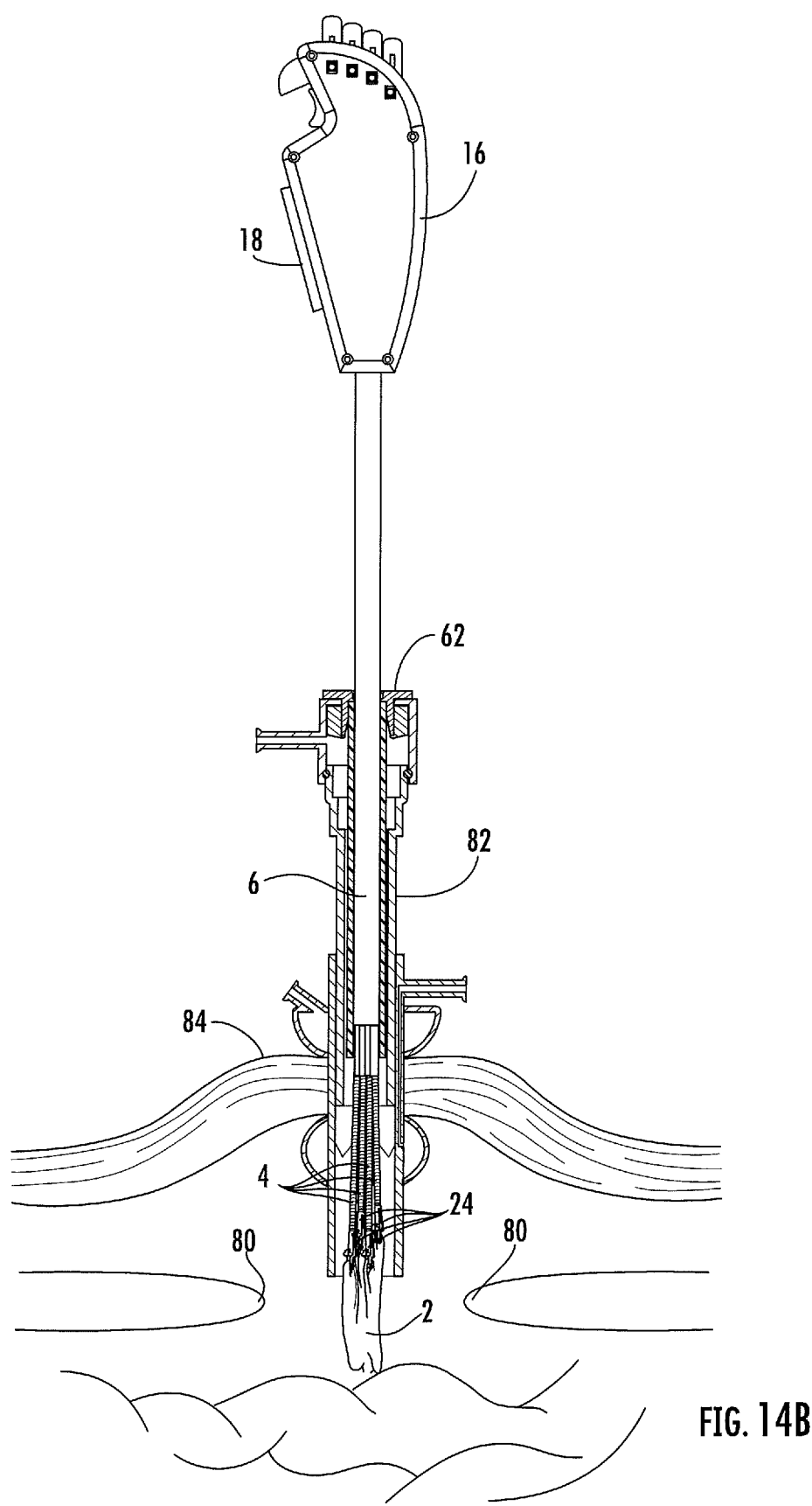
Figure 14C:
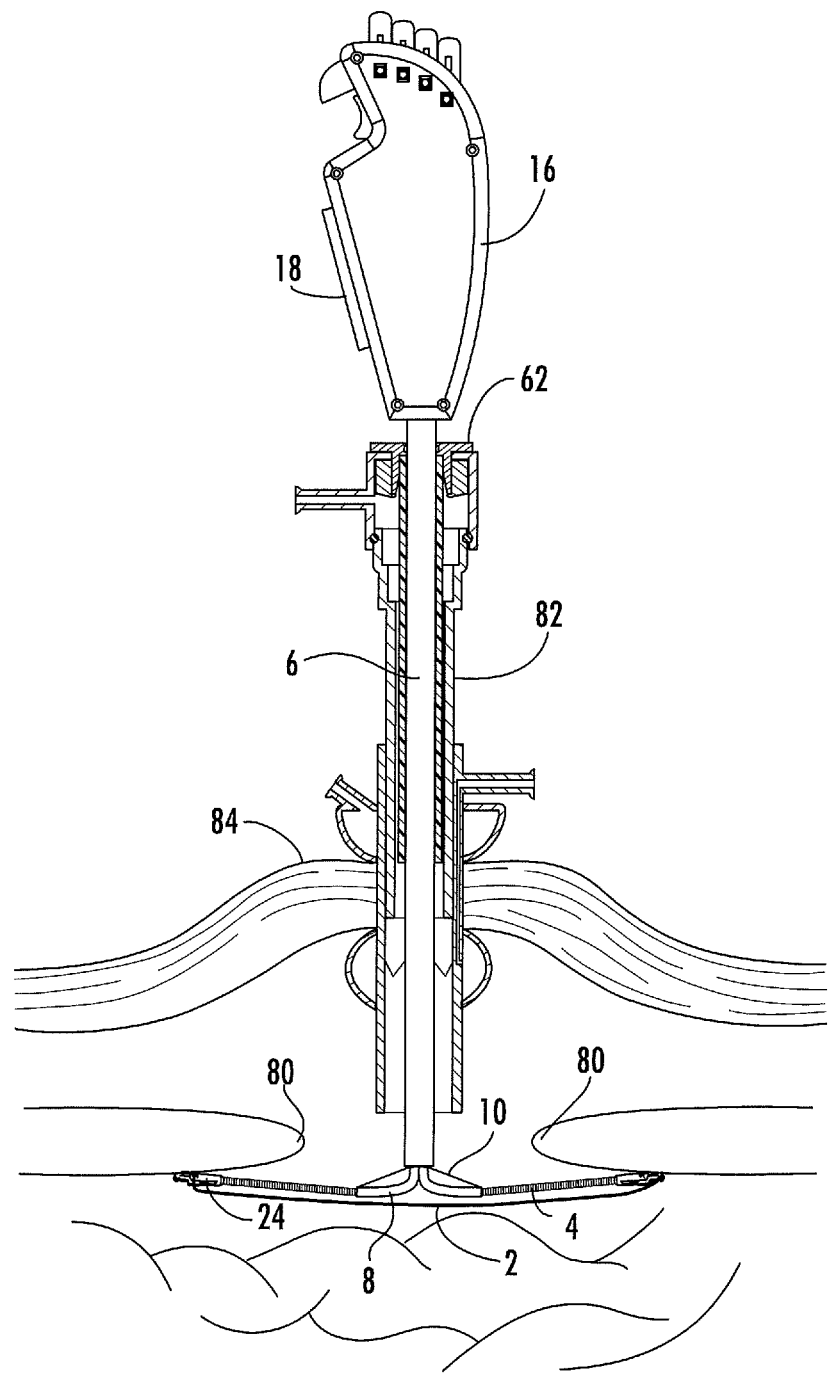

FIGS. 14A-14C demonstrate deployment of the graft through a trocar and into the surgical site using the device according to an embodiment of the device.

Figure 15:
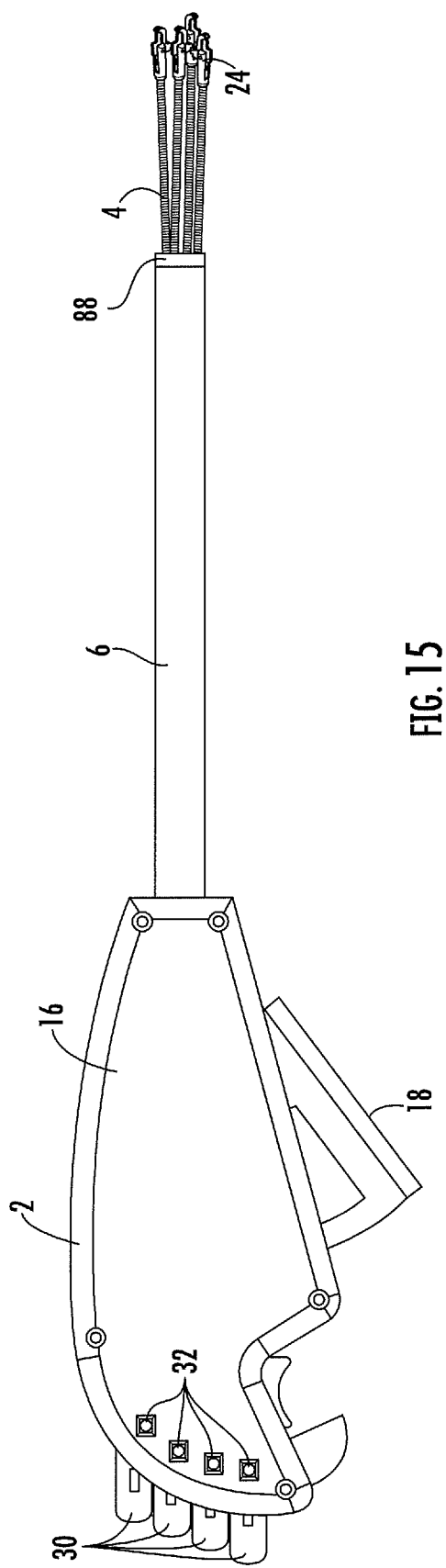

FIG. 15 is a side elevation of another embodiment of the device.

Figure 16:
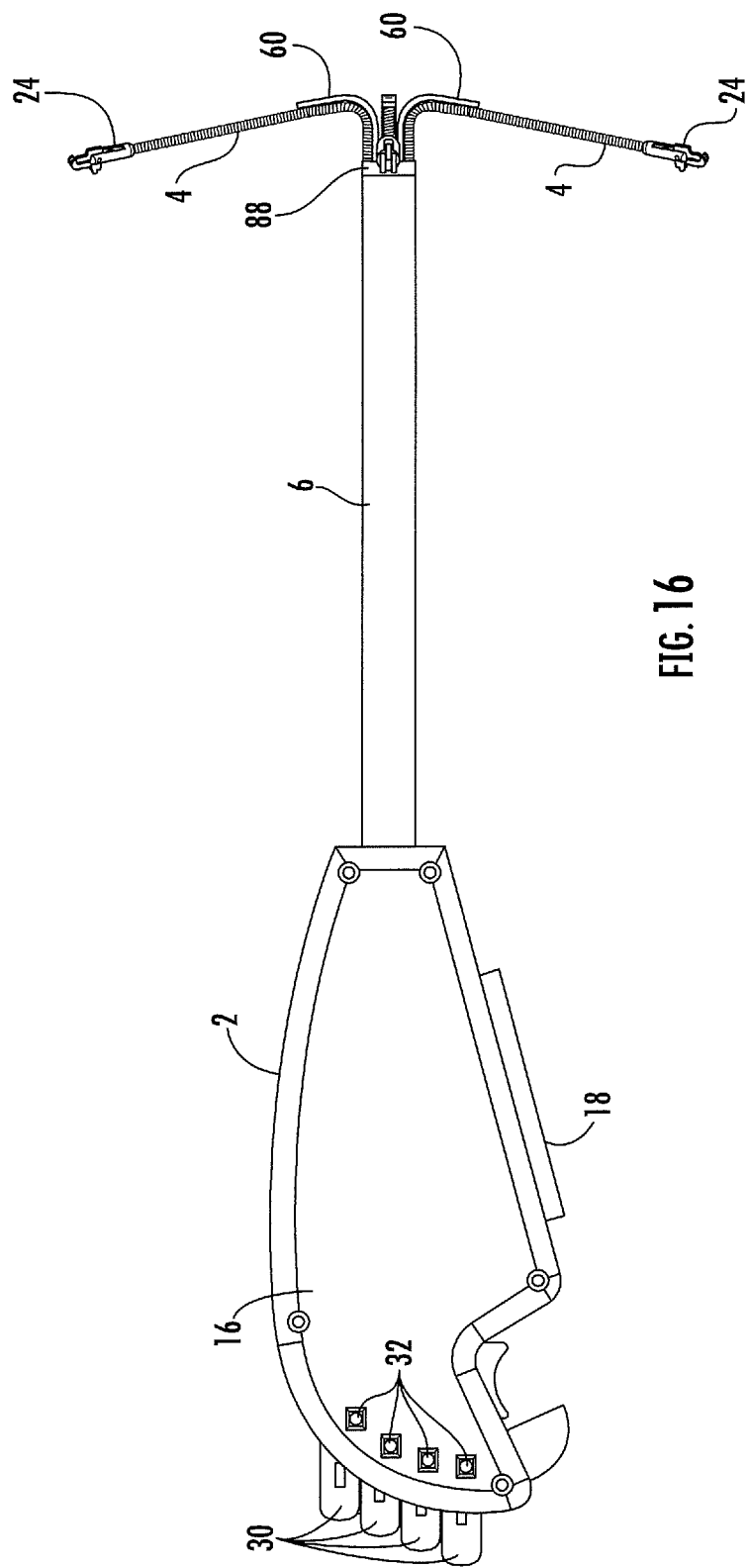

FIG. 16 shows the embodiment of FIG. 15 with the flexible arms 4 in a deployed position.

Figure 17:
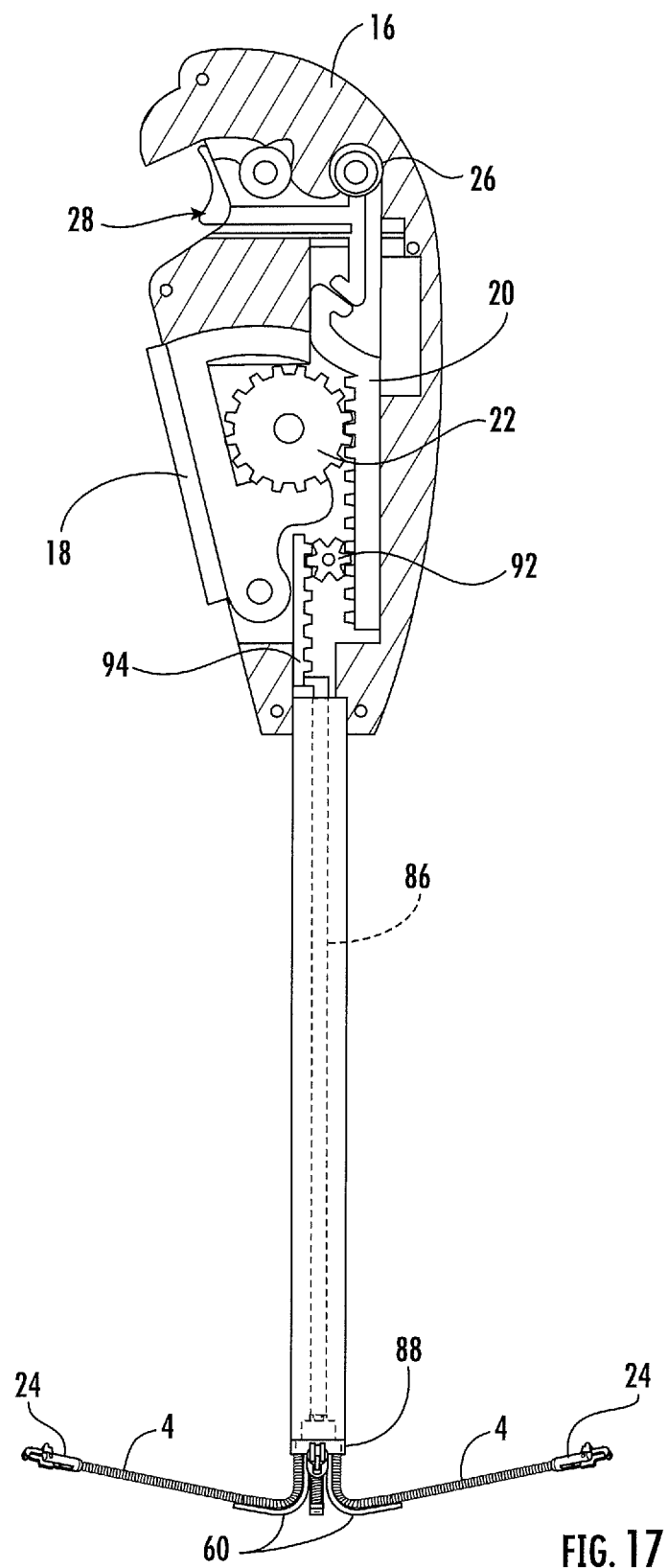

FIG. 17 is a partially sectioned view in an embodiment similar to that of FIG. 15 showing the actuation mechanism for extending and retracting the flexible arms with the flexible arms extended.

FIG. 18 is an isolation of deflectors extended from a tube or shaft of a housing.

FIG. 19 is an isolation of an arm extended from a tube or shaft of a housing.

FIG. 20 is an isolation of a flexible arm extended from a tube or shaft of a housing and deflectors extended from the housing, with the flexible arm deflected by a deflector to change the direction of the flexible arm.

DESCRIPTION OF PREFERRED EMBODIMENTS

Figure 1:
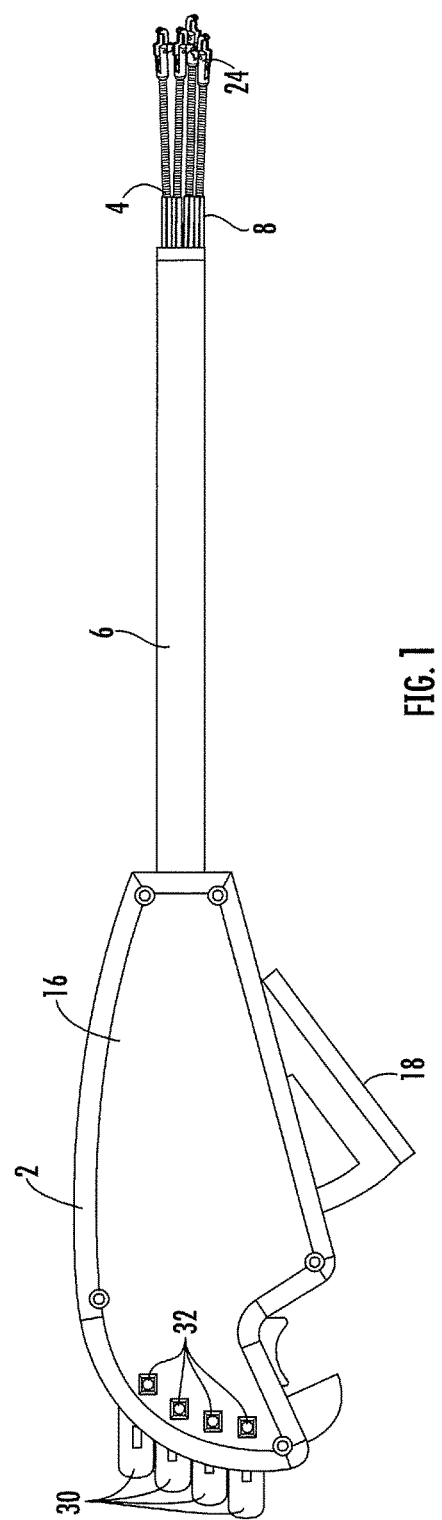
FIG. 1 is a side elevation of an embodiment of the invention.

Turning now to the drawing figures, FIG. 1 shows an embodiment of a delivery device for delivering a graft or synthetic mesh for attachment to tissue. The term "graft" is used herein to indicate either a graft formed of biological material, or a synthetic mesh. The graft is connected to a plurality of flexible arms 4. The flexible arms as shown in FIG. 1 extend from in a tube or shaft 6. The flexible arms are shown as being generally parallel to a central axis of the shaft. Since the flexible arms are flexible, some bending of the flexible arms means that they may not be strictly parallel, but are generally parallel, to the axis of travel of the rack 22 of the actuator while the flexible arms are in the position shown in FIG. 1.

Figure 2:
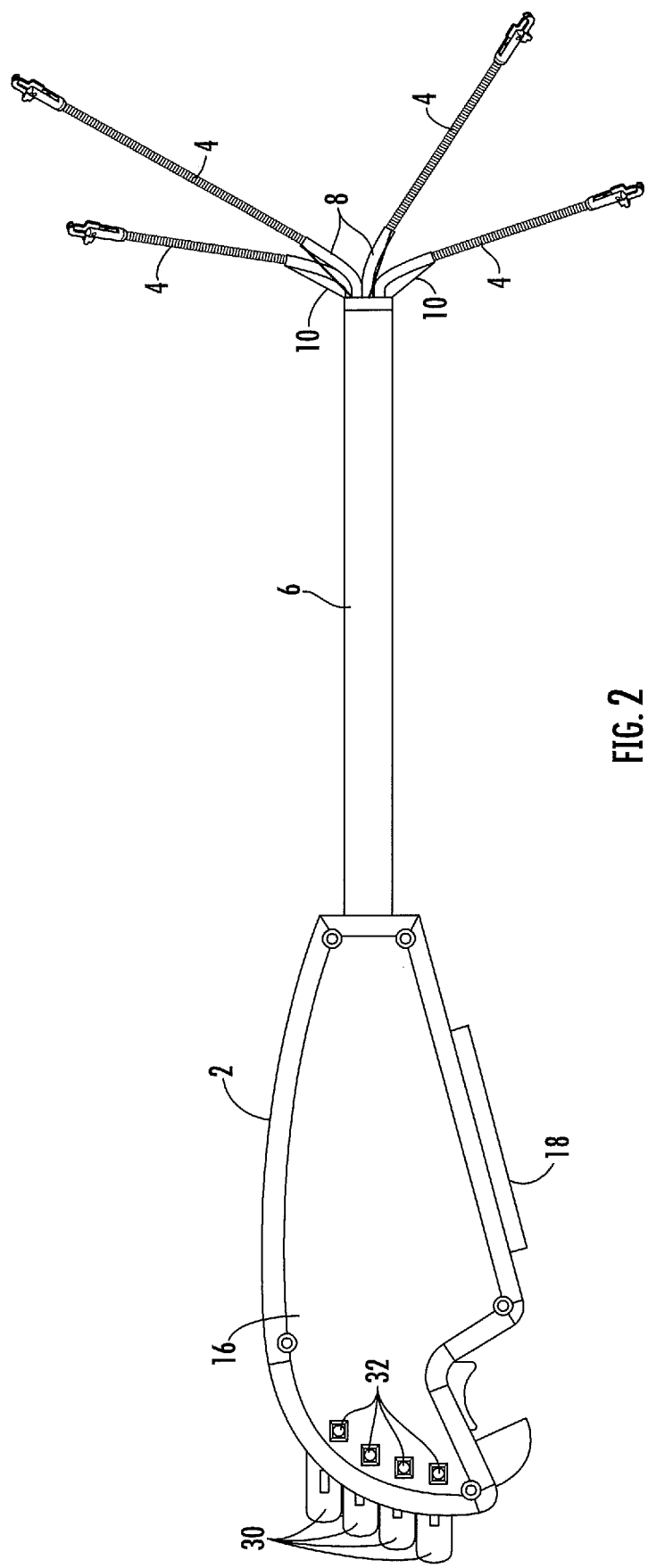
FIG. 2 shows the embodiment of FIG. 1 with the flexible arms 4 in a deployed position.

FIG. 1 and FIG. 2 show the device for delivery of graft for attachment to tissue, according to an embodiment, prior to deployment of the graft. Control wires 10 are actuated to pull against sleeves 8 that surround a portion of the flexible arms 4. The control wires extend through the shaft but may be external to the flexible arms as shown in FIG. 1 and FIG. 2, or they may be internal to the flexible arms. The control wires are connected to the sleeves at or near a distal end of the sleeves and control wires. In a preferred embodiment, each of the plurality of control wires is associated with one of the plurality of the flexible arms. Upon actuation, the control wires pull against the sleeves at the point of attachment to the sleeves. The force of the control wires acting on the sleeves pulls the flexible arms from the position shown in FIG. 1 and into a radial array as demonstrated in FIG. 2. The control wires are preferred to be nitinol wires, but the control wires may be formed of other metals, or plastics, textile materials or polymers, or similar materials having sufficient strength and flexibility.

As used herein, "proximal" is closest to the operator of the device and "distal" will typically be away from the operator and toward the patient when the device is in use.

Figure 4A:
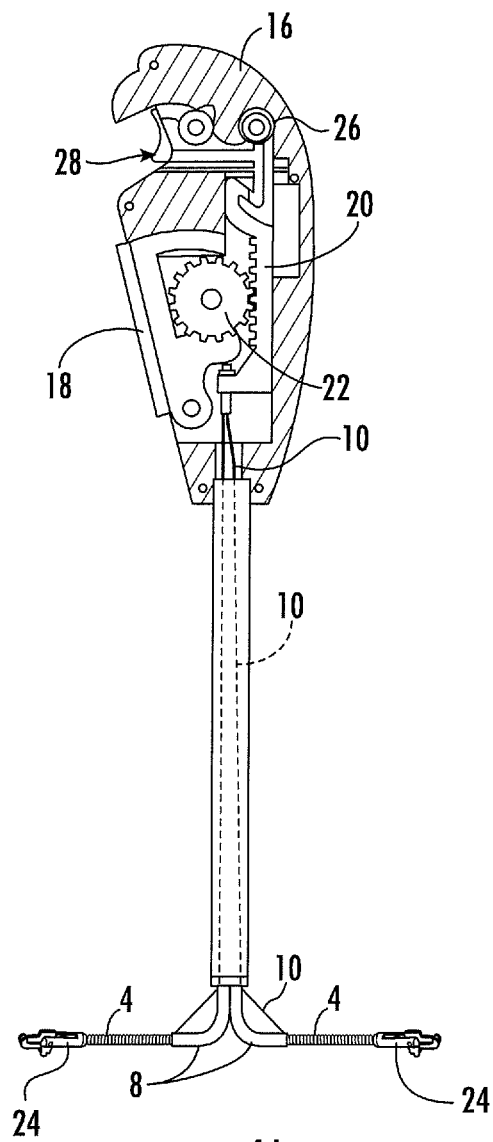
FIG. 4A is a partially sectioned view in an embodiment similar to that of FIG. 1 showing the actuation mechanism for extending and retracting the flexible arms with the flexible arms extended.
Figure 4B:
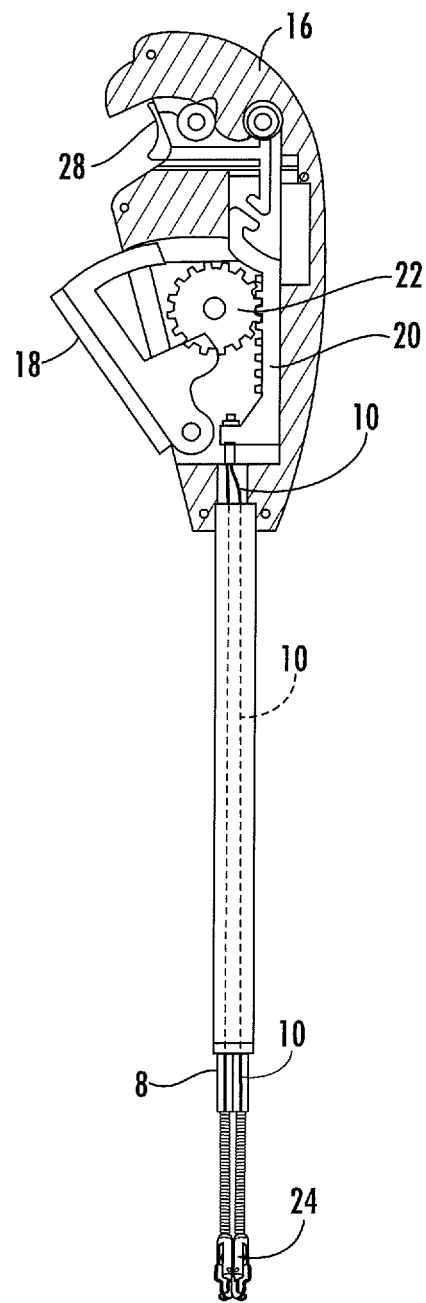
FIG. 4B is a partially sectioned view of the embodiment of the invention shown in FIG. 4A with the flexible arms retracted.

The actuator construct shown in FIG. 4A and FIG. 4B pulls the control wires 10, moving the flexible arms 4 to form a radial array (FIG. 2). This action unfolds the graft to a spread and generally planar position. In a preferred embodiment, when the travel of the actuator lever 18 is fully exhausted, the flexible arms may be positioned at an angle of somewhat more than 90° from the axis of travel of the actuator, or the central axis of the shaft. FIG. 14 shows the flexible arms as positioned at an angle of more than 90° from the central axis of the shaft. In some embodiments, this angle could be up to 120° from the generally parallel position of the flexible arms shown in FIG. 1. The actuator may be designed to allow the operator to set the desired angle. In some embodiments, the angle may be at least 100° and perhaps more, so that the edges, or periphery, of the graft are pulled against the defect of the patient for subsequent securing or suturing of the graft.

According to one embodiment of the invention, the device may comprise a housing 16 having a trigger or actuator lever 18. The housing may form a housing for the mechanism of the invention, including the actuator construct for the control wires 10. At the distal end of the device is the plurality of spaced-apart flexible arms 4 that terminate at the connectors for the graft, which may be grasping jaws 24.

The flexible arms 4 are preferred to be formed of a flexible cable. The cable may be a hollow cable formed of coiled or spirally-wound material which is capable of repetitive flexing and bending. The cable may comprise stainless steel suitable for use in surgical applications. The cables are sufficiently flexible to form the radial array shown in FIG. 2 when a force is applied by the control wires to the sleeves 8, but return to a flaccid condition as shown in FIG. 1 as the control wires cease pulling the flexible arms to the radial array. The flexible arms are preferred to be flexible along their entire length, without having preformed bends or angles that may tend to dictate a path of travel as the flexible arms are withdrawn from the surgical site. The flexible cables used with the sleeves (that are also flexible) and the control wires allow the cables to follow the anatomical structure or host tissue, or a trocar, as a path of travel as the flexible arms are pulled away from the graft. The sleeves may also be formed of hollow cable that is constructed and arranged to surround the flexible arms as shown in the drawing figures. Rigid members, rather than flexible cables, may tend to resist removal, due to anatomical structure or host tissue interfering with the path of travel. The flexible arms and the sleeves are preferred to have shape memory that allows them to return to about the shape shown in FIG. 1 or FIG. 14A when the control wires are not actuated to apply a force upon the flexible arms, The embodiment as shown in FIGS. 1 and 2 has four (4) flexible arms 4. At least three (3), and preferably four (4) or more, flexible arms are employed. The flexible arms must be able to deploy and spread out the graft for attachment to tissue as shown in FIG. 14C.

The flexible arms are formed in a radial array by force applied by the plurality of control wires 10. One control wire is associated with each flexible arm. The control wires pull against the sleeves 8 and the flexible arms to form the radial array. FIG. 2. As shown in FIG. 1, the flexible arms are substantially parallel to each other as they extend from shaft 6 of housing 16. No substantial tension is applied to the control wires in this configuration. The device with graft attached may be inserted into the surgical site incision in this configuration.

In FIG. 2, the control wires 10 are actuated to pull against the sleeves 8, forming the flexible arms 4 into a radial array. In use, the graft 2 is positioned on the flexible arms and the graft expanded for attachment by movement of the flexible arms into the radial array.

In an embodiment as shown in FIGS. 4A and 4B, the control wires are actuated simultaneously by the actuator construct contained in housing 16. An actuation lever 18 engages and rotates the ideal gear 22. The ideal gear 22 moves the rack gear 20 upwardly, applying a pulling pressure to the control wires 10 to form the flexible arms into the radial array. The ideal gear and the rack gear form a rack and pinion construct.

Latch 26 has interlocking members that engage with each other to hold the flexible arms in the radial array when the rack gear reaches its fully upward position. The interlocking members each comprises hook that interlocks with the corresponding hook. The graft is thereby held in a position for surgical attachment. A flexible arm release lever 28 pushes an interlocking member of the latch away from an interlocking member that may be formed on the rack gear 20 to release the control wires. With no tension or pulling force on the control wires, the flexible arms return to generally the position of FIG. 1. With tension released on the control wires, the flexible arms may be withdrawn through a trocar and/or surgical incision.

Figure 3:
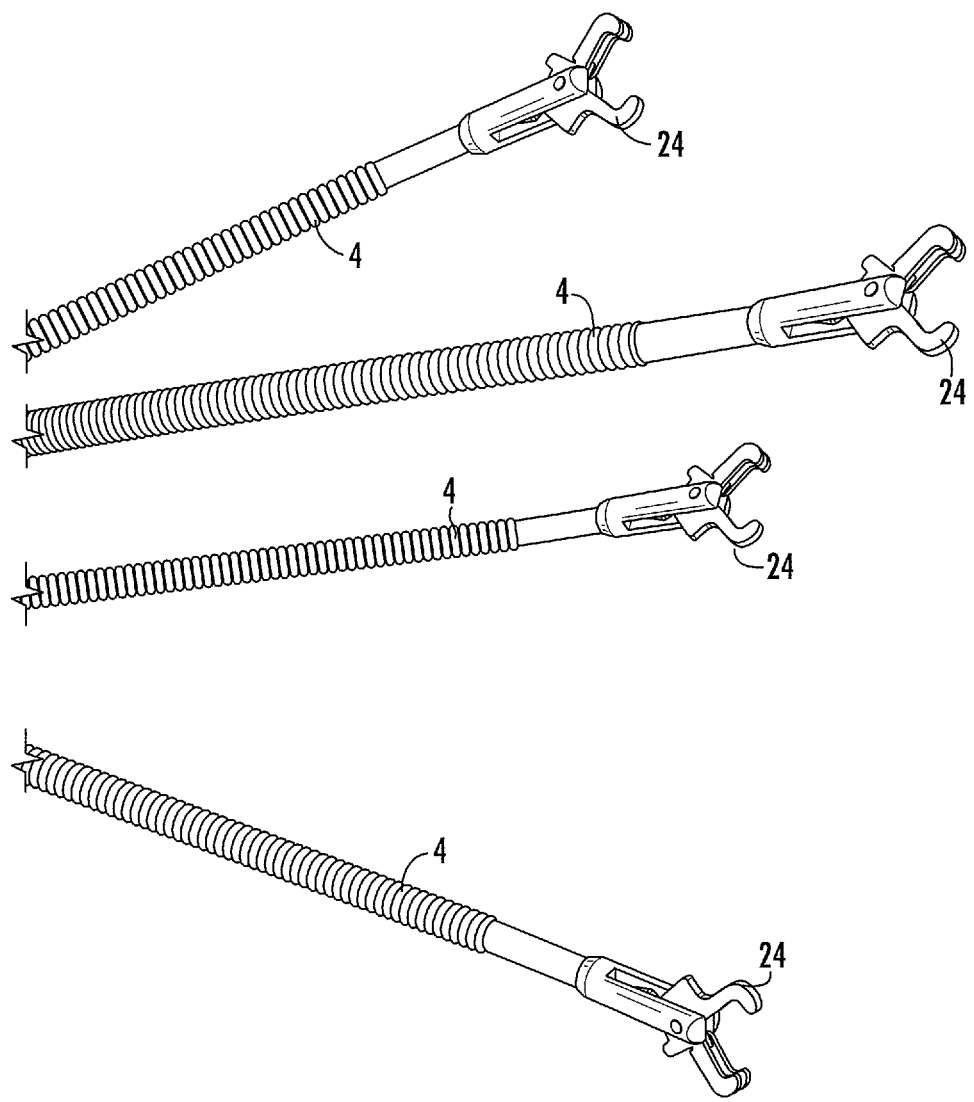
FIG. 3 shows flexible arms of the embodiment of FIG. 1 with the grasping jaws 24 at an end of each flexible arm in an open position for receiving a graft.

In the embodiment of the device shown in FIGS. 1 through 3, connectors 24 are positioned at or near the end of the flexible arms and are used to hold the graft for deployment. The connectors close upon the graft 2 to hold the graft. The connectors may be in the form of grasping jaws 24 in one embodiment that are actuated to close and open by pulling and releasing a connector strand, which may be a wire activation cable, or pull wire 56. A connector actuator construct as shown in FIG. 7, FIG. 8 and FIG. 10 communicates with the pull wire to open and close the connectors or grasping jaws for attachment and release of the graft. The connector actuator comprises a shuttle 40 in a preferred embodiment that ends with a control button 30 that extends from an end of the housing. The control button may be unitary with the shuttle, since depressing the control button (FIG. 8) moves the shuttle to open the connectors or grasping jaws. In this embodiment, each control button and shuttle is associated with one flexible arm 4 and its associated grasping jaw. Each control button is associated with one grasping jaw. Actuating, or depressing, a control button associated with a grasping jaw causes it to open. Preferably, the control buttons are formed to individually lock the grasping jaws in an open position when the control button in depressed (FIG. 3).

Figure 5:
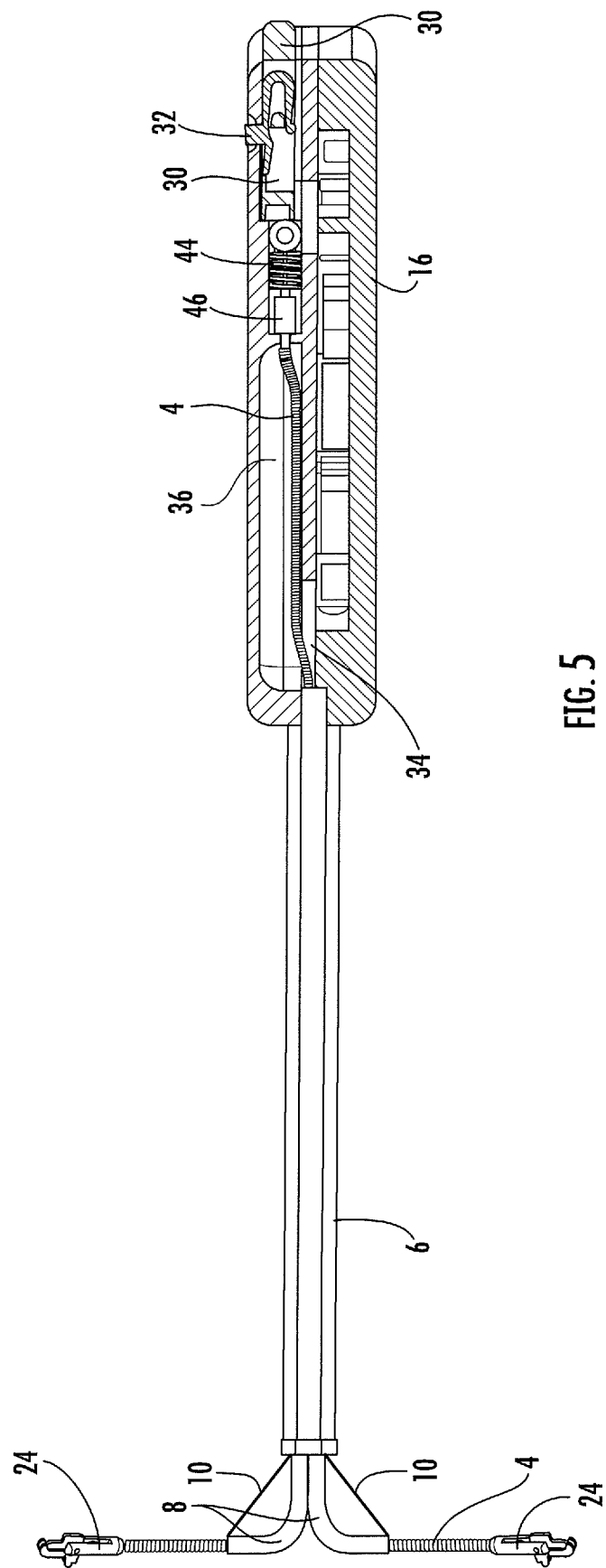
FIG. 5 is a sectioned view of an embodiment of the invention showing actuators in housing 16.

FIG. 5 is a top, sectioned view of the housing 16, showing two compartments, with one compartment on each side. The compartments may be separated by a divider 34. The lower compartment of the housing, when viewing FIG. 5, contains the mechanism of FIG. 4A and FIG. 4B and applies a force to sleeves 8 by control wires 10. This mechanism actuates the flexible arms 4 to pull the flexible arms into the radial array, or release the flexible arms.

The upper side of the housing as shown in FIG. 5 has a cavity 36 to store a portion of the flexible arms as the length of the flexible arms is adjusted for the specific application of a graft. The length of the flexible arms 4 may be adjusted by manually pulling or pushing the flexible arms into or out of the housing 16. Cavity 36 of the housing stores excess length of the flexible arms. The length adjustment feature is useful to adjust the size of the arm array to the dimensions, and particularly the perimeter, of the graft, so that the radial array of the device fits the graft and pulls the graft tight, but not tight enough to deform the flexible arms of the radial array. A frictional braking device 38 (FIG. 6B) is preferred to be positioned near the entry/exit of the cavity 36 of the housing to apply friction to the flexible arms. The frictional braking device applies friction to each flexible arm that is sufficient to allow a length of each of the flexible arms to be pushed into or pulled from the housing, while preventing unwanted withdrawal or insertion of the flexible arms relative to the housing. The frictional braking device may be opposing sheets of vinyl, rubber, or similar compressible materials through which the flexible arms pass, and which applies a frictional force on the flexible arms. In a preferred embodiment, the frictional braking device has openings or conduits equal in number to the number of flexible arms. Each flexible arm engages one of the conduits and the conduit applies a frictional force to the flexible arm to retard but not prevent movement of the flexible arm into and out of the cavity as described. A cover of the housing may have protrusion(s) or boss(es) 72 formed thereon that applies pressure to deform the braking device and conduits for the application of frictional pressure to the flexible arms.

By the control wires 10 acting on the sleeves, with the flexible arms 4 being slidable relative to the sleeves 8, the length of the portion of the flexible arms that extend from the distal end of the device may be altered while still providing a workable mechanism for forming the radial array irrespective of the length of each flexible arm that is chosen.

Separate mechanisms are provided for controlling the length of the flexible arms and opening and closing of the grasping jaws on one side of the housing 16 and the actuation of the sleeves to form the radial array on the other side of the housing.

The graft 2 is attached about its perimeter to each of the flexible arms 4. The graft is attached at spaced apart intervals so that the graft is formed in a radial array when the control wires are actuated. A portion of the graft is inserted between each open connector, which is a grasping jaw 24 in the embodiment shown. After insertion of a portion of the graft into the open grasping jaw, the grasping jaw is closed by releasing tension on the connector strand to hold the graft. The control buttons 30 are released from their locked positions by one or more release buttons 32. FIG. 10A, 10B. In a preferred embodiment, the grasping jaws 24 each have a separate control button 30 and release button 32 so that the grasping jaws can each be independently opened and closed.

FIG. 7 shows housing 16 with flexible arms 4 attached to the grasping jaws 24, and extending from the cavity 36 of the housing and though shaft 6. This construct communicates with control buttons 30 to open the grasping jaws, which are normally closed. Anchor sites 46 for the flexible arms 4 are shown.

FIG. 8 is enlarged to show the detail of a preferred structure of the anchor sites. Shuttle 40 communicates with an associated control button 30 (not shown in this figure). A set screw 42 connects pull wire 56 to the shuttle. A compression spring 44 tensions the control wire to hold the grasping jaw closed. An anchoring collar 46 for the flexible arm is provided. Depressing release button 32 (FIG. 10B) allows the shuttle to be pushed proximally to compress the spring 44 and close the grasping jaws by providing tension on the pull wire.

FIG. 9 shows detail of an embodiment of the grasping jaws 24. The grasping jaws may have an upper tooth 48 and a lower tooth 50 as shown, each of which pivot about a pivot pin 52. The upper tooth and the lower tooth may be housed in the jaw housing 54. A pair of pull wires 56 that may be internal to the flexible arm 4 contract to open and close. The grasping jaws are preferred to be normally closed. Springs 44 apply tension to the pull wires so that the grasping jaws are closed until the shuttle 40 via control buttons 30 push the springs forward to relieve tension on the pull wires.

FIGS. 10A, 10B show the interaction between an embodiment of the shuttle 40 and release button 32. As shown in FIG. 10A, the shuttle is pushed forward by pressing control button 30. This action depresses spring 44 and opens the grasping jaw. An end of release button 32 engages an opening in the shuttle due to shape memory properties of the release button, locking the shuttle in place with the grasping jaw open.

Depressing release button 32 disengages the end of the release button. Spring 44 causes the shuttle to move from the position of FIG. 10A to the position of FIG. 10B. Expanded spring 44 applies tension to the pull wires 56 to close the grasping jaws 24. In the embodiment shown, a release button 32 is provided for each flexible arm and associated grasping jaw. However, a bridge could be provided so that the grasping jaws may be universally closed at once. After the grasping jaws are closed on the graft 2, the graft is held in place by the grasping jaws 24. After surgical attachment of the graft, the control buttons are actuated to release the graft from the grasping jaws. The control wires 10 are also released from tension by the actuator construct, and the device is removed through the surgical site incision.

FIG. 12 demonstrates the graft being attached to the device. The grasper jaws are opened using the control buttons 30. In this embodiment, the graft is connected at four (4) points to the flexible arms using the grasper jaws and generally about the perimeter of the graft. The grasper jaws are closed on the graft to hold the graft. The actuator is used to place the flexible arms in an orientation with the flexible arms generally parallel to each other for insertion through a trocar and into the surgical site.

A sheath 64 for facilitating insertion of the flexible arms and graft into the trocar and to the surgical site is shown. FIGS. 13A-13D. The sheath in this embodiment is a split tube that may be transparent or translucent. The sheath is preferred to be tapered, or have a frusto-conical shape that tapers or progressively reduces in diameter from left to right when viewed as in the drawing figures. A stand 68 holds an end of the sheath open at the split. A bullet shaped tool 66 having a diameter that is larger than the middle of the sheath may be used to slide from the end of the sheath that is adjacent to the stand and along the sheath to the opposite end, forcing the sheath to open about the split. FIG. 13B. The sheath is open at the split to a width that permits insertion of the flexible arms and the graft. The sheath, attached to the device, is placed into the sheath through the split. The sheath and the device are removed from the stand for insertion into a trocar.

FIGS. 11A, 14A show a seal 62 mounted to the shaft 6. The seal engages the trocar and the shaft to form a seal, inhibiting gasses from escaping the belly of the patient. FIG. 14B. An O-ring may be present about a circumference 70 of the seal to improve sealing.

FIGS. 15-20 depict a second embodiment of the device. The second embodiment operates essentially the same as the embodiment described above, excepting that the arms are formed into a radial array by deflectors 60.

The second embodiment incorporates flexible arms 4 that extend from the tube or shaft 6 of the housing 16. The length of the arms may be varied as described above. The graft is positioned on, and detached from, connectors 24 controlled as described herein. The device is used as described herein except that movement of the flexible arms into a radial array is accomplished by deflectors 60 rather than control wires 10.

A plurality of deflectors 60 are used to redirect the flexible arms 4 into a radial array. FIG. 16. Each deflector corresponds to one of the plurality of flexible arms. Each deflector is formed of shape memory material. The deflectors may be formed of nitinol. The deflectors, when not constrained by end cap 88, form an angle of about 90°. As shown, the deflectors form an angle that causes the arms to travel slightly more than 90° from their generally side by side configuration.

The deflectors 60 are in communication with an actuator, and move in response to movement of the actuator. The actuator may comprise actuation lever 18, ideal gear 22, rack gear 94, and rack gear 20 as described above. The actuator moves linkage 86 in response to the actuation lever to advance and retract the deflectors 60. As shown in the drawings, the direction of travel of the linkage when the actuator is engaged is opposite the direction of travel initiated by the actuator construct in the embodiment that uses control wires. Idler gear 92 is positioned between rack gear 20 and rack gear 94 to achieve the direction of travel to push the deflectors distally to deflect.

Pressing the actuation lever 18 advances the deflectors out of the end cap, whereupon the shape memory properties of the deflectors causes the distal ends of the deflectors to assume a radial array. FIG. 18. Each deflector contacts one flexible arm 24 and deflects the arm laterally, and substantially at 90° to form the flexible arms into a radial array. FIG. 16; FIG. 20. The flexible arms extend past the distal ends of the plurality of deflectors when the plurality of arms is fully extended from the housing.

The deflectors 60 are retractable, and may be retracted into an end cap 88 present in the end of the shaft of the housing. The end cap forms the deflectors into a generally side by side configuration as the deflectors are retracted into the end cap. FIG. 19. This configuration allows the arms and the deflectors to be withdrawn from the surgical site, as the arms and deflectors are positioned in the side by side configuration, with the device having the construct generally as shown in FIG. 15. The actuation lever is positioned as shown in FIG. 15 so that the linkage 86 has pulled the deflectors into the end cap. Each of the deflectors exits a void in the end cap that is adjacent to a void in the end cap from which an associated flexible arm 24 exits the end cap, so that contact of the deflector with its associated arm is assured. Each deflector is associated with one flexible arm.

In use, according to one embodiment, a section of graft 2 of appropriate size to repair the subject hernia is selected and/or formed. FIG. 12. The graft may be formed (of various biological materials or, synthetic materials, including, but not limited to polypropylene or polytetrafluoroethylene (PTFE). The graft is connected near its perimeter to the connectors near the distal ends of the flexible arms. Each flexible arm is preferred to have a connector, such as grasping jaws 24. The actuation lever 18 is in the position shown in FIG. 1 or FIG. 15, with the flexible arms positioned generally parallel to the axis of travel of the actuator. The graft is held by the flexible arms and folded. The graft is preferred to be covered by the sheath 64 for insertion into the trocar.

An incision in tissue 84 of the patient is made at the approximate center of the defect. Preferably, a trocar 82 is present within the incision. FIGS. 14A-C. The flexible arms of the device in a generally parallel orientation are inserted through the approximate center of the defect. FIG. 14A. The sheath 64 facilitates insertion of the graft 2 into the trocar, and protects the graft as it moves through the trocar to the surgical site. FIG. 14B. After the distal end of the device with graft attached travels through the trocar, and sufficient clearance through the defect 80 is obtained, the actuator, such as the gear train of FIG. 4A, is actuated causing the actuator to pull the control wires 10, the flexible arms 4 and associated graft to the position shown in FIG. 14. The graft is pulled up against the tissue by means of the handle of the device to cover the hernia defect 80. Graft attachment to the tissue may be provided by known methods of attachment of grafts at surgical sites such as hernia defects. The procedure may be monitored by use of a laparoscope for proper positioning, and securing, of the graft. In the embodiment shown in FIGS. 15-20, after the distal end of the device with graft attached travels through the trocar, and sufficient clearance through the defect 80 is obtained, the actuator, such as the gear train of FIG. 17, is actuated causing the deflectors 60 to deflect the flexible arms 4 in FIG. 16.

The graft 2 is formed to generally a planar form when the flexible arms 4 form the radial array. As noted, the flexible arms may move through an arc that is more than 90°. Therefore, the surface of the graft may be somewhat curved or non-planar, so that the edges or periphery of the graft is pushed against the tissue and secured to the tissue to cover the defect. However, the graft is still considered to be in a generally planar position.

After the connectors 24 are released from the graft 2 as described above, tension is released from the control wires 10 or the deflectors 60 are withdrawn into the end cap 88. The flexible arms 4 return to the position shown in FIG. 1, FIG. 14A, FIG. 15. The device may now be removed by pulling it upwardly through the trocar and away from the incision. The flexible arms, by being flexible along their length, with no preformed angles, kinks or similar geometry, are sufficiently flexible to follow a path of retreat from the fully extended position of FIG. 2 to the position shown in FIG. 1, without disrupting the sutured graft, while also being sufficiently rigid to support the graft for positioning and securement at the defect site.

What is claimed is:

1. A device for delivery of a graft for attachment to tissue, comprising:
    a plurality of flexible arms;
    a plurality of deflectors formed of shape memory material, wherein the normal shape of each deflector of the plurality of deflectors forms substantially a right angle at a distal portion of the plurality of deflectors relative to a proximal portion of the plurality of deflectors, wherein each flexible arm of the plurality of flexible arms is associated with a deflector of the plurality of deflectors;
    an actuator comprising a linkage, wherein the plurality of deflectors is in communication with the linkage and the linkage is configured to move in response to the actuator;
    wherein the linkage is configured to push the plurality of deflectors from a channel that forms the plurality of deflectors into a substantially straight shape, and the linkage is configured to advance the plurality of deflectors from the channel to enable each of the deflectors of the plurality of deflectors to form the normal shape;
    wherein the plurality of deflectors form their normal shape and contact the plurality of flexible arms to form the distal ends of the plurality of flexible arms to spread away from each other to form a radial array.

2. A device for delivery of a graft for attachment to tissue as described in claim 1, wherein a length of each flexible arm of the plurality of flexible arms is individually adjustable and each flexible arm of the plurality of flexible arms is slidable relative to a deflector of the plurality of deflectors with which the flexible arm is associated, wherein a length of a first arm of the plurality of flexible arms is differentiated from a length of a second arm of the plurality of flexible arms.

3. A device for delivery of a graft for attachment to tissue as described in claim 1, further comprising a brake, wherein each flexible arm of the plurality of flexible arms frictionally engages the brake, and wherein the brake permits the plurality of flexible arms to slide to permit individual adjustability of the plurality of flexible arms, and the brake is configured to resist sliding of the plurality of flexible arms.

4. A device for delivery of a graft for attachment to tissue as described in claim 1 further comprising a brake, wherein the brake comprises a plurality of channels formed therein, and each flexible arm of the plurality of flexible arms frictionally engages a channel of the plurality of channels of the brake, and wherein the brake permits the plurality of flexible arms to slide to permit individual adjustability of the plurality of flexible arms and the brake is configured to resist sliding of the plurality of flexible arms.

5. A device for delivery of a graft for attachment to tissue as described in claim 1, wherein a portion of each flexible arm of the plurality of flexible arms is slidable into a chamber of a housing, and wherein the actuator is contained in the housing.

6. A device for delivery of a graft for attachment to tissue as described in claim 1,
    wherein the plurality of flexible arms comprises three flexible arms and the plurality of deflectors comprises three deflectors,
    wherein each flexible arm of the three flexible arms comprises a connector at the distal end, and
    wherein each connector is constructed to open and close, and each connector is constructed to close on a graft, and the three flexible arms hold the graft in the radial array when the linkage advances the plurality of deflectors.

7. A device for delivery of a graft for attachment to tissue as described claim 1,
    wherein the plurality of flexible arms comprises three flexible arms, wherein each flexible arm of the three flexible arms comprises a connector at the distal end, and
    wherein each connector is constructed to open and close, and each connector is constructed to close on a graft, and the connectors and the three flexible arms hold the graft in the radial array when the linkage advances the plurality of deflectors, and
    wherein each connector of each flexible arm of the three flexible arms is constructed to open and close separately from every other connector.

8. A device for delivery of a graft for attachment to tissue as described claim 1,
    wherein the plurality of flexible arms comprises three flexible arms, wherein each flexible arm of the three flexible arms comprises a connector at the distal end, and
    wherein each connector is constructed to open and close, and each connector is constructed to close on a graft, and the connectors and the three flexible arms hold the graft in the radial array when the linkage advances the plurality of deflectors, and
    wherein each connector of each flexible arm of the three flexible arms is constructed to open and close separately from every other connector, and
    a housing in which the actuator is contained comprises three connector actuators, wherein closing of each connector is remotely actuated by a corresponding connector actuator of the three connector actuators, and each of the three connector actuators operates independently of each of the other connector actuators.

9. A device for delivery of a graft for attachment to tissue as described in claim 1,
    wherein the plurality of flexible arms comprises three flexible arms, wherein each flexible arm of the three flexible arms comprises a connector at the distal end, and
    wherein each connector is constructed to open and close, and each connector is constructed to close on a graft, and the connectors and the three flexible arms hold the graft in the radial array when the linkage advances the plurality of deflectors, and
    wherein each connector of each flexible arm of the three flexible arms is constructed to open and close separately from every other connector, and
    a housing in which the actuator is contained comprises three connector actuators, wherein opening of each connector is remotely actuated by a corresponding connector actuator of the three connector actuators, and each of the three connector actuators operates independently of each of the other connector actuators, and wherein the housing comprises a release actuator, wherein the release actuator actuates tension on a connector linkage and causes the connector to close.

10. A device for delivery of a graft for attachment to tissue as described in claim 1, wherein the actuator comprises a rack and pinion, and rotation of the pinion by a lever actuates movement of the rack, and wherein the rack communicates with the plurality of flexible arms and movement of the rack is configured to advance the linkage to move the plurality of deflectors to form the plurality, of flexible arms into the radial array.

11. A device for delivery of a graft for attachment to tissue as described in claim 1, further comprising a sheath positioned at an end of a shaft, the sheath having a longitudinal split along a length thereof, wherein the sheath is constructed to accommodate and surround the distal ends of the plurality of flexible arms, with the plurality of flexible arms positioned generally parallel to each other, and with a graft connected to the plurality of flexible arms.

12. A device for delivery of a graft for attachment to tissue as described in claim 1, the plurality of flexible arms comprising three flexible arms and a connector at the distal end, wherein each connector is constructed to open and close, and each connector is constructed to close on a graft, the device for delivery of a graft for attachment to tissue further comprising a sheath having a longitudinal split along a length thereof, wherein the sheath is constructed to accommodate and surround the distal end of each of the three flexible arms and a graft connected to the three flexible arms; and wherein the distal ends of each of the three flexible arms are positioned within the sheath in a generally parallel relationship, and the sheath is constructed and arranged to be inserted into a trocar.

13. A device for delivery of a graft for attachment to tissue as described in claim 1, wherein the channel is present in a cap positioned at an end of a shaft that surrounds the linkage.

14. A device for delivery of a graft for attachment to tissue as described in claim 1, wherein a length of each flexible arm of the plurality of flexible arms is independent of a length of the deflector of the plurality of deflectors with which the flexible arm is associated.

15. A device for delivery of a graft for attachment to tissue as described in claim 1, wherein the plurality of flexible arms are positioned in a side by side relationship with each other when the plurality of deflectors are formed in the substantially straight shape.

16. A device for delivery of a graft for attachment to tissue as described in claim 1, wherein the shape memory material that forms the plurality of deflectors comprises nitinol.

\* \* \* \* \*